US00PP26353P3

(12) United States Plant Patent
Klemm et al.

(10) Patent No.: US PP26,353 P3
(45) Date of Patent: Jan. 26, 2016

(54) ***DAHLIA* PLANT NAMED 'KLEDH13037'**

(50) Latin Name: ***Dahlia* sp.**
Varietal Denomination: KLEDH13037

(71) Applicant: Klemm+Sohn GmbH & Co. KG, Stuttgart (DE)

(72) Inventors: Nils Klemm, Stuttgart (DE); Silke Wagener, Leinfelden-Echterdingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 115 days.

(21) Appl. No.: 14/120,252

(22) Filed: May 13, 2014

(65) Prior Publication Data
US 2015/0334899 P1 Nov. 19, 2015

(51) Int. Cl.
*A01H 5/00* (2006.01)

(52) U.S. Cl.
USPC ..... Plt./321

(58) Field of Classification Search
USPC ..... Plt./321
See application file for complete search history.

*Primary Examiner* — Annette Para
(74) *Attorney, Agent, or Firm* — Barbara Campbell; Bethany R. Roahrig; Cochran Freund & Young, LLC

(57) ABSTRACT

A new *Dahlia* plant particularly distinguished by a dark-red flower color, a compact, and semi-upright habit and good basal branching, is disclosed.

2 Drawing Sheets

Genus and species: *Dahlia* sp.
Variety denomination: 'KLEDH13037'.

BACKGROUND OF THE NEW PLANT

The present invention comprises a new and distinct variety of *Dahlia*, botanically known as *Dahlia* sp., and hereinafter referred to by the variety name 'KLEDH13037'. 'KLEDH13037' originated from an open-pollination conducted in Summer 2009 in Stuttgart, Germany between the proprietary female *Dahlia* variety 'DH-2009-0559' (unpatented) and an unknown male *Dahlia* variety (unpatented).

The seeds from the open-pollination were sown and plants were grown in a greenhouse for evaluation, where an individual plant designated 'KLEDH13037' was selected from the group in May 2010 of plants in Stuttgart, Germany. In May 2010, 'KLEDH13037' was first vegetatively propagated by unrooted cuttings. 'KLEDH13037' was found to reproduce true to type in successive generations of asexual propagation via unrooted cuttings.

SUMMARY

The following are the most outstanding and distinguishing characteristics of this new variety when grown under normal horticultural practices in Stuttgart, Germany.

1. Dark-red flower color;
2. A compact, and semi-upright habit and
3. Good basal branching.

DESCRIPTION OF THE PHOTOGRAPHS

This new *Dahlia* plant is illustrated by the accompanying photographs of the variety grown in a glass greenhouse in Stuttgart, Germany and taken in March 2014. The colors shown are as true as can be reasonably obtained by conventional photographic procedures.

DESCRIPTION OF THE NEW VARIETY

Figure 1:
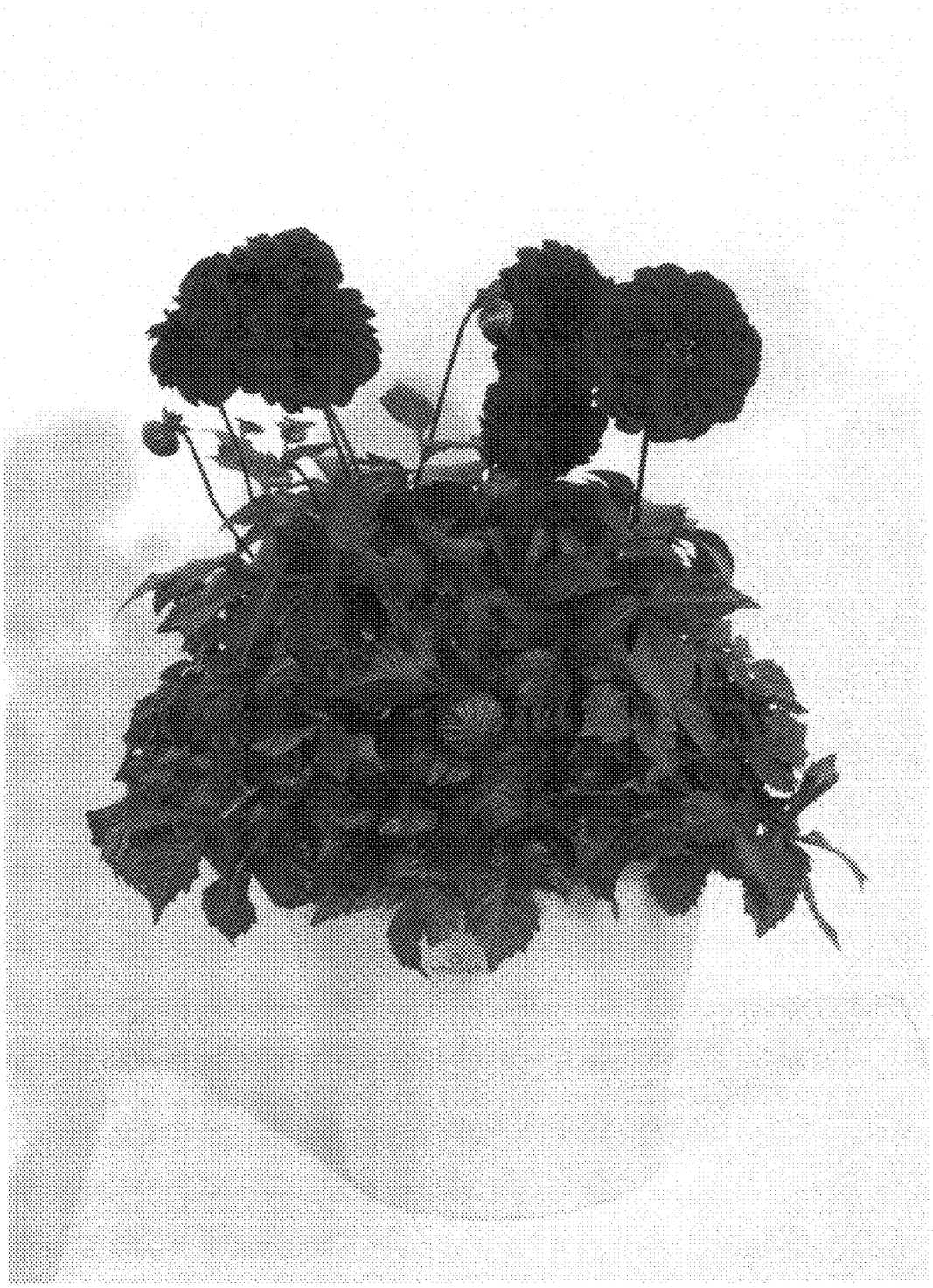
FIG. 1 shows the foliage, habit, and flowers of a 3-month old plant grown in a pot.
Figure 2:
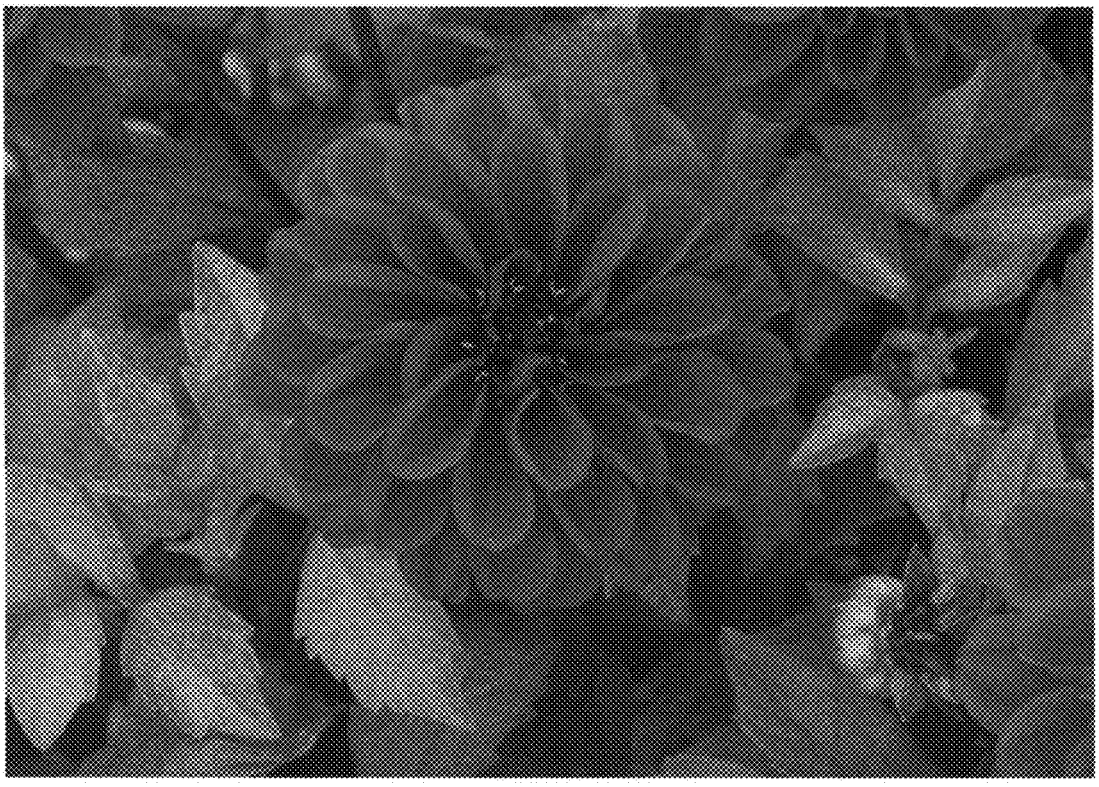
FIG. 2 shows a close-up of the ray florets and disc florets of a mature flower of a plant about 5-months old.

The following detailed descriptions set forth the distinctive characteristics of 'KLEDH13037'. The data which define these characteristics were collected from asexual reproductions carried out in Stuttgart, Germany. Data was collected on 4-month old plants grown in a controlled greenhouse environment approximating those generally used in commercial production, pinched once, with a growth regulator, and under natural and artificial light. Color references are to The R.H.S. Colour Chart of The Royal Horticultural Society of London (R.H.S.), $5^{th}$ edition (2007).

Classification:
- *Family*.—Asteraceae.
- *Botanical*.—*Dahlia* sp.
- *Common*.—*Dahlia*.
- *Designation*.—'KLEDH13037'.

Parentage:
- *Female parent*.—The proprietary female *Dahlia* variety 'DH-2009-0559' (unpatented).
- *Male parent*.—An unknown male *Dahlia* variety (unpatented).

Plant:
- *Plant and growth habit*.—Compact, semi-upright, free basal branching, and inflorescences held above the foliar plane.
- *Height*.—20.0 cm to 25.0 cm.
- *Diameter*.—35.0 cm to 40.0 cm.

*Propagation*.—Unrooted cuttings.
*Time to produce a rooted young plant*.—3 to 4 weeks.
*Root description*.—Medium thickness and light tan in color.
*Rooting habit*.—Freely branching and moderately dense.

Lateral branches:
*Length*.—About 15.0 cm.
*Diameter*.—About 1.0 cm.
*Internode length*.—About 1.0 cm to 2.0 cm.
*Aspect*.—Outwardly spreading; about 30 degrees from vertical.
*Strength*.—Strong.
*Texture*.—Smooth.
*Color*.—RHS N77.

Foliage/leaves:
*Arrangement*.—Leaves are opposite, 3 to 5 leaflets per leaf, pinnately compound.
*Length*.—Up to 19.0 cm.
*Width*.—Up to 23.0 cm.
*Shape*.—Ovate to elliptic.
*Apex*.—Acute.
*Base*.—Acute.
*Margin*.—Serrate.
*Immature leaf color*.—Upper surface: RHS 141A. Lower surface: RHS 141C.
*Mature leaf color*.—Upper surface: RHS 136A. Lower surface: RHS 136C.
*Texture* (*both upper and lower surfaces*).—Pilose.
*Venation pattern*.—Pinnate.
*Venation color* (*both surfaces*).—RHS 136A; sometimes anthocyanin is present but is mainly on the basal leaves on the upper surfaces.
*Petioles*.—Length: 5.0 cm up to the first leaflet pair; about 4.0 cm up to the second leaflet pair. Diameter: About 0.5 cm. Texture: Upper surface: Smooth. Lower surface: Smooth, but sparsely covered with hairs. Color: Upper surface: RHS 59A. Lower surface: RHS 143C.

Buds:
*Height*.—About 1.0 cm.
*Diameter*.—About 1.5 cm to 2.0 cm.
*Shape*.—Oblate.
*Color*.—RHS 59A and RHS 143B towards the base.

Inflorescence:
*Appearance and arrangement*.—Daisy-eyed double inflorescences held above the foliar plane.
*Fragrance*.—Absent.
*Time to flower*.—In the winter, about 3 months after planting; in the summer, about 2 months after planting.
*Post-production longevity*.—Plants flower continuously from spring through autumn.
*Inflorescence diameter*.—About 9.0 cm.
*Inflorescence depth*.—About 6.0 cm.
*Disc diameter*.—About 1.5 cm.
*Receptacle height*.—About 1.0 cm.
*Receptacle diameter*.—About 3.5 cm.
*Receptacle color*.—RHS 144B and RHS 59A towards the tips.

Ray florets:
*Quantity per inflorescence*.—About 70 arranged in about 6 whorls.
*Length*.—4.0 cm.
*Width*.—3.0 cm.
*Shape*.—Ovate to oblate.
*Apex*.—Obtuse.
*Base*.—Rounded.
*Margin*.—Entire.
*Aspect*.—Semi-upright.
*Texture* (*both upper and lower surfaces*).—Smooth.
*Color, immature*.—Upper surface: RHS 53A to RHS 59A. Lower surface: RHS 59B.
*Color, mature*.—Upper surface: RHS 53A. Lower surface: RHS 59B.

Disc florets:
*Quantity per inflorescence*.—About 60.
*Length*.—About 1.0 cm.
*Diameter*.—0.2 cm.
*Shape*.—Tubular.
*Texture* (*both the upper and lower surfaces*).—Smooth.
*Color, both mature and immature, both upper and lower surfaces*.—RHS N77A.

Phyllaries:
*Quantity per inflorescence*.—4 to 5.
*Length*.—About 1.0 cm.
*Width*.—About 1.0 cm.
*Shape*.—Ovate.
*Apex*.—Acute.
*Base*.—Rounded to truncate.
*Margin*.—Absent.
*Texture* (*both upper and lower surfaces*).—Smooth.
*Color*.—Upper surface: RHS 143A; anthocyanin at the basal end or all over the surface. Lower surface: RHS 143A.

Peduncles:
*Length, terminal peduncle*.—Up to 18.0 cm.
*Length, axillary peduncle*.—Up to 18.0 cm.
*Diameter*.—0.4 cm.
*Aspect*.—Semi-upright.
*Strength*.—Strong.
*Texture*.—Smooth.
*Color*.—RHS N77A.

Reproductive organs:
*Androecium*.—Present on only fully developed on disc florets. Quantity per floret: 4 to 5. Filament length: About 0.6 cm. Filament color: RHS 3C. Anther shape: Lanceolate. Anther length: 0.5 cm. Anther color: RHS 15A. Pollen amount: Abundant. Pollen color: RHS 21A.
*Gynoecium*.—Quantity per floret: 1. Pistil length: 1.0 cm. Style length: 0.4 cm. Style color: RHS 1D. Stigma shape: Lanceolate pinnate. Stigma color: RHS 7A. Ovary color: RHS 154C.

Fruit and seed set: No fruit and seed set observed.

Disease and pest/insect resistance: No disease and pest/insect resistance observed.

COMPARISON WITH PARENTAL LINE AND KNOWN VARIETY

'KLEDH13037' is a distinct variety of *Dahlia* and is distinguished from its parents as described in Table 1.

TABLE 1

| Comparison with Parental Lines | | |
|---|---|---|
| Characteristic | 'KLEDH13037' | Female Parent 'DH-2009-0559' |
| Branching | Better basal branching than 'DH-2009-0559' | Less basal branching than 'KLEDH13037' |

'KLEDH13037' is a distinct variety of *Dahlia* and is most similar to the commercial *Dahlia* variety 'Dalaya Raja' (also known as 'KLEDH13034', unpatented). Differences between the varieties are described in Table 2.

TABLE 2

| Comparison with Similar Variety | | |
|---|---|---|
| Characteristic | 'KLEDH13037' | 'Dalaya Raja' |
| Flower color, of ray florets | Dark red | Purple |

We claim:

1. A new and distinct variety of *Dahlia* plant designated 'KLEDH13037' as shown and described herein.

* * * * *